US007679375B2

(12) United States Patent
Merkel (10) Patent No.: US 7,679,375 B2
(45) Date of Patent: Mar. 16, 2010

(54) SYSTEM AND METHOD FOR DETECTING FOREIGN OBJECTS IN A PRODUCT

(75) Inventor: Harald Merkel, Lindome (SE)

(73) Assignee: Food Radar System in Sweden AB, Gothenburg (SE)

( * ) Notice: Subject to any disclaimer, the term of this patent is extended or adjusted under 35 U.S.C. 154(b) by 132 days.

(21) Appl. No.: 11/884,445

(22) PCT Filed: Feb. 17, 2006

(86) PCT No.: PCT/SE2006/000218

§ 371 (c)(1),
(2), (4) Date: Apr. 30, 2008

(87) PCT Pub. No.: WO2006/088423

PCT Pub. Date: Aug. 24, 2006

(65) Prior Publication Data

US 2009/0052764 A1    Feb. 26, 2009

(30) Foreign Application Priority Data

Feb. 18, 2005    (SE)    .................................... 0500385

(51) Int. Cl.
*G01R 27/04* (2006.01)
(52) U.S. Cl. ........................ 324/639; 73/1.82
(58) Field of Classification Search ......... 324/637–646; 73/1.82
See application file for complete search history.

(56) References Cited

U.S. PATENT DOCUMENTS 3,910,124 A    10/1975    Halsey

| 5,132,623 | A | * | 7/1992 | De et al. ..................... 324/338 |
| 6,065,376 | A | | 5/2000 | Khachatoorian |
| 6,456,093 | B1 | | 9/2002 | Merkel et al. |
| 6,645,144 | B1 | | 11/2003 | Wen et al. |
| 7,190,176 | B2 | * | 3/2007 | France ......................... 324/639 |
| 7,221,169 | B2 | * | 5/2007 | Jean et al. .................... 324/639 |

FOREIGN PATENT DOCUMENTS

WO    WO-01/20311 A1    3/2001

* cited by examiner

*Primary Examiner*—Vincent Q Nguyen
(74) *Attorney, Agent, or Firm*—Birch, Stewart, Kolasch & Birch, LLP (57) ABSTRACT

A system for detecting a change in material composition in a product including a microwave transmitter emitting a microwave signal at a predetermined microwave frequency composition, and an ultrasonic transmitter emitting an ultrasound signal at a predetermined ultrasound frequency composition into at least a part of the product to create a density displacement within the product. The system further includes a receiver to receive a microwave signal and/or an ultrasonic signal passed through at least apart of the product, device to measure the attenuation and/or runtime between each emitted signal and each received signal, respectively, under the influence of the created density displacement, and a comparator to compare the measured attenuation and/or runtime with a previously determined attenuation and/or runtime to determine a change in material composition to detect a possible change in material composition in a product.

15 Claims, 6 Drawing Sheets

SYSTEM AND METHOD FOR DETECTING FOREIGN OBJECTS IN A PRODUCT

TECHNICAL FIELD

The present invention relates to a system for detecting a change in material composition in a product. The invention also relates to a method for detecting a possible change in material composition in a product.

BACKGROUND TO THE INVENTION

The term foreign bodies comprises all solid materials that are undesired in products, especially food products, originating from the product or not, such as bone fragments, bits of glass, rubber, gravel/stone, hair, insects, etc.

In the international application published as WO01/20311, an apparatus for detection of foreign bodies in materials is disclosed which is fast, non-invasive and non-destructive. Electromagnetic signals having at least two different frequencies pass through the material and the transmitted and received signals are analyzed and compared to a predetermined reference value, obtained from a reference sample, for each frequency. A presence of a foreign object in the material will create a difference in damping and/or phase shift between the material and the reference sample.

A drawback of the prior art is that the described method only measures the dielectric property $\in$, which means that it is difficult to detect a foreign object in a material if the dielectric contrast between the object and the material is small.

Further drawbacks with the described method is that the resolution of the method is limited by the microwave wavelength, which in some cases results in a too small resolution, and increasing frequency reduces the wavelength and therefore increases the resolution at the cost of a limited penetration depth. The antenna patterns used in the apparatus are sensitive to adjacent products, which leads to crosstalk. Furthermore, measurement results are inherently temperature dependent.

Furthermore, the U.S. Pat. No. 3,910,124 A discloses a system including two different energy sources, viz. at least one microwave transmitter and at least one ultrasonic transmitter. The energies emitted from these different sources are said to complement each other in that the ultrasonic energy is sensitive to laminar conditions while microwave energy is sensitive to density changes, in the search for intra part or subsurface anomalies. Also, it is stated that ultrasonic energy penetrates a metal component with greater facility, while microwave energy will penetrate any non-metal component.

However, still, the mere complementary use of microwave and ultrasonic energies will not increase the resolution while maintaining a sufficient penetration depth in order to achieve the desired detection of a change in material composition, such as foreign bodies in food products.

SUMMARY OF THE INVENTION

An object with the invention is to provide a system and a method for detection of foreign objects in material, especially food products, which overcome the above mentioned drawbacks.

The object is achieved in a system as defined in claim 1, and in a method as defined in claim 9.

An advantage with the present invention is that more orthogonal data is obtained including acousto-electric data, which depends on an inherently different mechanism, compared to the prior art.

Another advantage is that the resolution is given by the smallest wavelength of the used signals, i.e. the wavelength of the ultrasonic signal.

Still another advantage with the present invention is that objects without $\in$-contrast can be detected by the applied ultrasonic signal.

Still another advantage with the present invention is that it is immune to surrounding objects since the ultrasonic wave is coupled only mechanically.

DETAILED DESCRIPTION OF THE PREFERRED EMBODIMENTS

Figure 1:
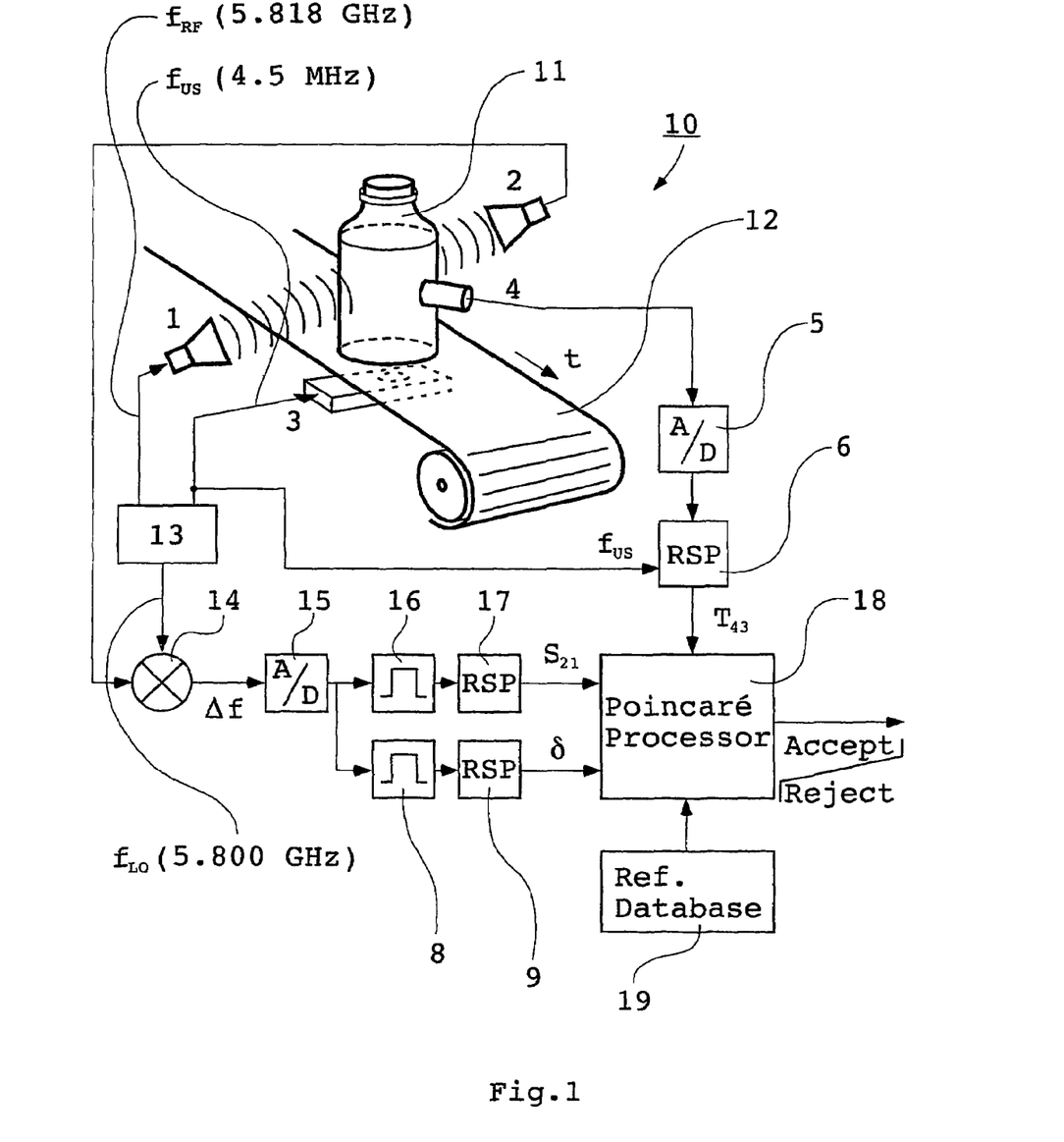
FIG. 1 shows a first embodiment of the system according to the present invention.

FIG. 1 shows a first embodiment of a system 10 according to the invention. A filled glass jar 11, which is the product under examination, is in this example placed on a conveyor belt 12 and moved through a measurement gap. The system 10 comprises a microwave part, an ultrasonic part and an evaluation part. The system comprises in this embodiment two fixed-frequency microwave generators and a fixed frequency ultrasonic generator arranged in a signal generator device 13. The first microwave generator has a first fixed microwave frequency $f_{RF}$ (e.g. 5.818 GHz) and is coupled to at least one transmit antenna 1, and the second microwave generator has a second fixed microwave frequency $f_{LO}$ (e.g. 5.800 GHz) and is preferably coupled to a down converter 14, such as a mixer. The down converter shifts the transmitted microwave signal, which is collected by at least one receive antenna 2, and the received microwave signal from the second microwave generator to a low intermediate frequency IF. This allows the microwave signal transmitted through the product under test 11 to be evaluated in amplitude and phase. Thus, a signal having a difference frequency $\Delta f$ (i.e. 5.818 GHz-5.800 GHz=18 MHz) is fed from the mixer 14 and fed into an analogue/digital converter 15.

The system further comprises a filter unit 16, a set of signal processors RSP 17 and an evaluation processor, a so-called Poincaré processor 18 that contains necessary algorithms to control the system and to evaluate the data. The result from the evaluation processor 18 is either to accept or to reject the product 11. The system 10 also comprises at least one ultrasonic transducer 3, in addition to the transmit antenna 1 and receive antenna 2, all grouped around the measurement gap. The transducer 3 is in mechanical contact with the conveyor belt 12 and emits an ultrasonic signal having an ultrasonic frequency composition including a frequency $f_{US}$ (e.g. 4.5 MHz) through the product 11. This causes a density displacement travelling at ultrasonic speed. At the same time, a microwave signal from the first microwave generator is emitted from the transmit antenna 1. This signal also travels through the product 11, though at a much higher speed. The microwave signal exhibits damping and phase delay by travelling through the product leaving the microwave frequency unchanged. In those volumes of the product 11 where the ultrasonic wave creates a slowly propagating density displacement, a part of the microwave signal is shifted in frequency and upper and lower side-bands are created. The transmitted microwave signal is collected using the microwave receive antenna 2. The received signal is down converted using the down converter unit 14. The low frequency signal is then analogue/digital converted using the ADC 15 and bandpass filtered in the filter unit 16. The digital signal is filter processed using the receive signal processor RSP 16. The receive signal processor RSP converts the incoming digital signal into zero frequency using standard state-of-the-art digital filters.

The outcome of this filtering corresponds to the $S_{21}$ parameter, which is not shifted in frequency, between the transmit 1 and receive 2 antenna as is well known to those skilled in the art. Alternatively, we may refer to the receive antenna 1 as microwave port 2 and the transmit antenna 2 as a microwave port 1.

In the system described herein, there is a second set of bandpass filters 8 and a second digital signal processor RSP 9 connected in parallel to the first signal path 16, 17.

The first bandpass filter 16 is tuned to the difference frequency between the both microwave generators and, in the pre-sent embodiment being 5.818 GHz-5.800 GHz=18 MHz. The second set of bandpass filters 8 is tuned to sum of the difference frequency between the microwave generators (e.g. 18 MHz) and the centre frequency (e.g. 4.5 MHz) of the ultrasonic signal generator. Therefore, this second digital signal processor path, containing the filters 8 and the processor 9, converts the incoming signal to zero frequency that has been shifted in frequency by the ultrasonic frequency. The measurement result is therefore limited to the cross sectional volume between the ultrasonic signal and the microwave signal, denoted $\delta$.

In this embodiment of the present invention, there is also an ultrasonic receiver 4 present which collects the ultrasonic radiation emitted from the transducer 3 and evaluates the damping, $T_{43}$, and the runtime, as described in more detail in the pending Swedish patent application SE0402788-4, assigned to Frigoscandia Equipment AB. Alternatively, we may refer to the ultrasound receiver 4 as port 4 and the transducer 3 as the port 3. The signal from the ultrasonic receiver 4 is fed to an analogue/digital converter 5, and the damping and runtime are calculated in an ultrasonic processing unit RSP 6, but this may of course be integrated in the evaluation unit 18.

Furthermore, a reference database 19 is accessible to the evaluation unit 18 to perform the method according to the invention, as will be described in connection with FIGS. 8 and 9.

Figure 2:
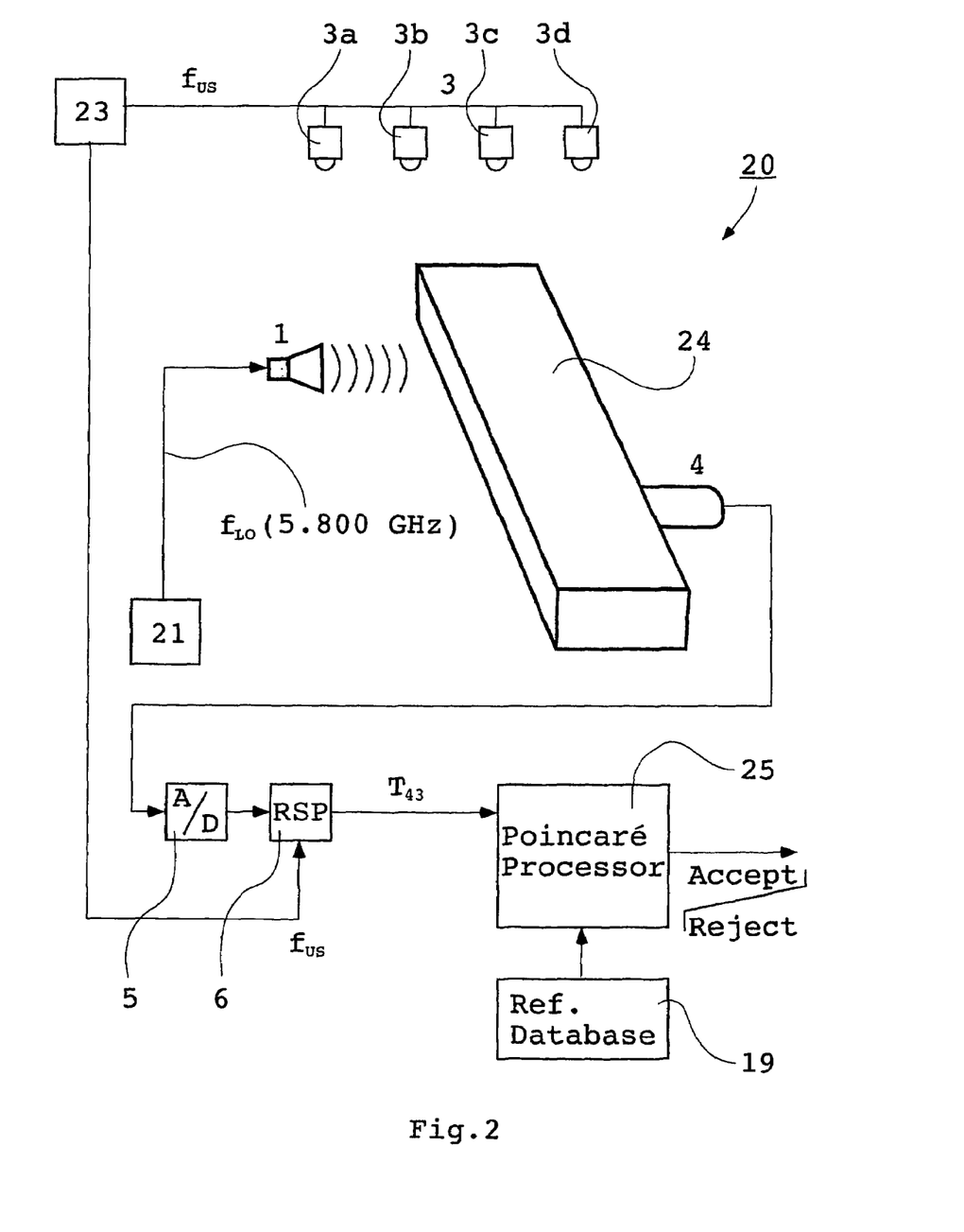
FIG. 2 shows a second embodiment of the system according to the present invention.

FIG. 2 shows a second embodiment of a system 20 comprising a first microwave antenna 1 that emits a microwave signal with a first fixed frequency $f_{RF}$, e.g. 5.800 GHz, as mentioned in connection with FIG. 1. The microwave signal is generated in a microwave generator 21. Several ultrasonic transducers 3a-d, which are commonly denoted 3, are connected to an ultrasonic generator 21 to generate an ultrasonic signal having an ultrasonic frequency $f_{US}$, e.g. 4.5 MHZ, as mentioned in connection with FIG. 1. The microwave signal, emitted from the first microwave antenna 1, is arranged to travel through a piece of material 24, which in this example represents the product under examination. An ultrasonic receiver 4 is mechanically attached to the material 24 to be able to receive an ultrasonic signal originating from the ultrasound transducers 3.

The piece of material 24 is not placed on a conveyor means, but instead the emitted ultrasonic signal from the ultrasonic transducers 3 is adapted to focus on different positions in the material in a predetermined way, as described in connection with FIGS. 5 and 6.

A measurement of the received ultrasonic signal at the ultrasonic receiver 4 is performed for each focal position of the emitted ultrasonic signal under the influence of an interaction with the transmitted microwave signal from the microwave transmitter 1. The received signal is fed to an analogue/digital converter 5, and the received signal is analysed in a signal processor RSP 6, as described in connection with FIG. 1. The result is a measurement of $T_{43}$ for each focal position of the emitted ultrasonic signal.

Figure 6:
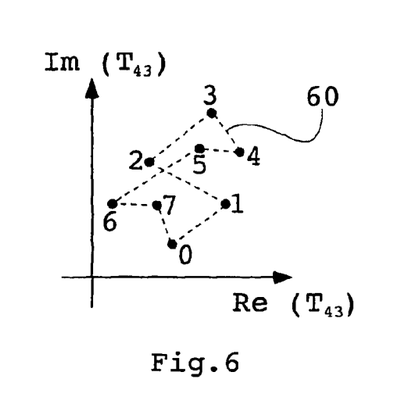
FIG. 6 shows a Poincaré curve generated by the method using the alternative function as illustrated in FIG. 5.

An evaluation unit 25 receives the values of $T_{43}$, which in this example is a complex variable, consisting of a real part $Re(T_{43})$ and an imaginary part $Im(T_{43})$ which represent a two-dimensional image of the product under examination as shown in FIG. 6. A reference database 19 is connected to the evaluation unit to provide information needed to perform the method, as will be described in connection with FIGS. 8 and 9. The output from the evaluation unit 25 is either "accept", if the measured values are acceptable, or "reject", if the measured values are unacceptable, in view of the values stored in the reference database 19.

In an alternative embodiment, the microwave transmitter 1 is moved in relation to the product under examination 24, while the emitted ultrasonic signal is not changing its focus. The result will be a continuously measured behaviour of $T_{43}$, and an image as shown in FIG. 4c can be created.

The important features of the present invention are that at least one microwave signal and at least one ultrasonic signal are transmitted into a product simultaneously. Further, at least one receiver, either an ultrasonic receiver and/or a microwave receiver, is used to measure the effect of the propagating density displacement inside the product.

Figure 3:
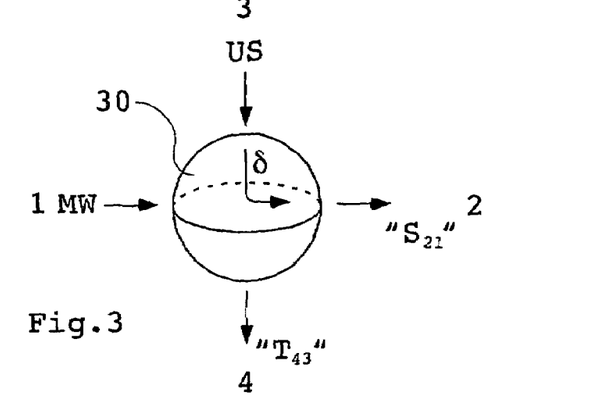
FIG. 3 illustrates the basic function of method according to the present invention.

FIG. 3 illustrates the basic principle of the method according to the invention. A product 30 is radiated with microwave radiation from a microwave transmitter 1 and ultrasonic radiation from an ultrasonic transducer 3. An ultrasonic receiver 4 will be able to determine the complex value $T_{43}$ as described in connection with FIGS. 1 and 2 using an analogue/digital converter 5 and a signal processor 6. A microwave receiver 2 will be able to determine the parameter $S_{21}$ as described in FIG. 1 using a mixer 14, an analogue/digital converter 15, a set of bandpass filters 16 and a signal processor 17. Furthermore, the acousto-electric effect $\delta$ may also be determined as described in FIG. 1 using the received microwave signal from the microwave receiver 2 using the mixer 14, the analogue/digital converter 15, the bandpass filters 8 and the signal processor 9.

Figure 4A:
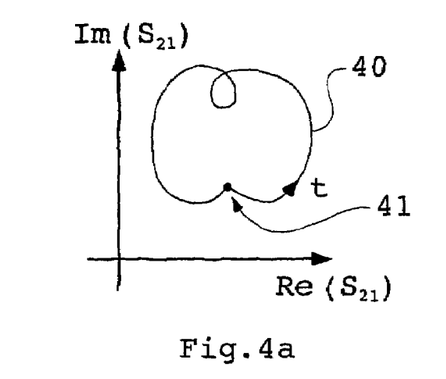
FIGS. 4a-4d show different Poincaré curves generated by the method using the basic function as illustrates in FIG. 3.
Figure 4B:
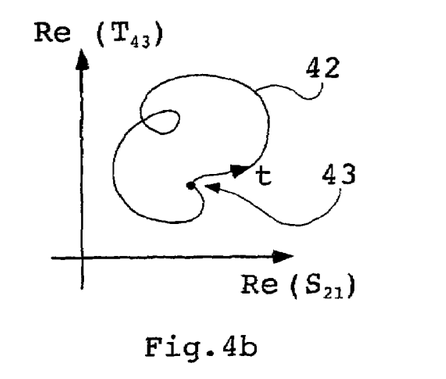
Figure 4C:
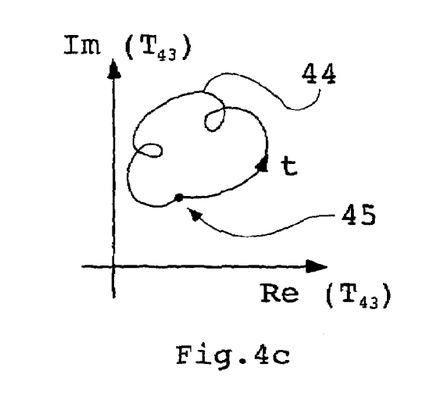

Two or more of these parameters may be used to create an image, such as a Poincaré curve, shown in FIGS. 4a-4d. In FIG. 4a, two parameters, $Re(S_{21})$ and $Im(S_{21})$, are used to create the Poincaré curve 40. The point 41 (t=0) on the curve 40 represents the occasion when no product is present in the measurement gap. As soon as a product enters the measurement gap, the transmitted ultrasonic signal will create a density displacement propagating inside the product and this will in turn effect the complex variable $S_{21}$ and change its value during the movement of the product through the gap. When the product has passed through the gap, the values of $Re(S_{21})$ and $Im(S_{21})$ will again be at point 41. This movement is illustrated in the figure by the arrow marked by a "t" on the curve 40 denotes the curve parameter being the position along the object under test or time assuming constant velocity of movement.

In FIG. 4*b*, a Poincaré curve 42 is shown that uses a different pair of parameters, $Re(S_{21})$ and $Re(T_{43})$. Point 43 represents the absence of a product in the measurement gap, as described above.

In FIG. 4*c*, a Poincaré curve 44 is shown that uses another pair of parameters, $Re(T_{43})$ and $Im(T_{43})$. Point 45 represents the absence of a product in the measurement gap, as described above.

Figure 4D:
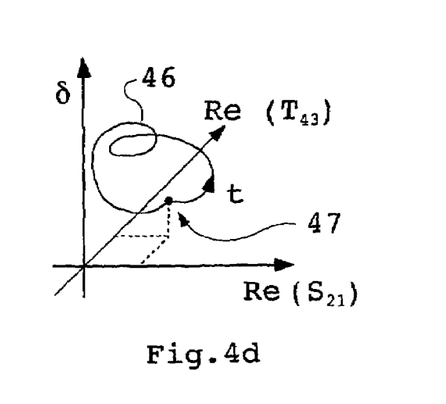

In FIG. 4*d*, a three-dimensional Poincaré curve 46 is shown that uses three parameters, $Re(S_{21})$, $Re(T_{43})$ and 6. Point 47 represents the absence of a product in the measurement gap, as described above.

It is of course possible to create a Poincaré curve using all five parameters, e.g. $Re(S_{21})$, $Im(S_{21})$, $Re(T_{43})$, $Im(T_{43})$ and 5, but such a five-dimensional curve is not illustrated in the drawings.

Figure 5:
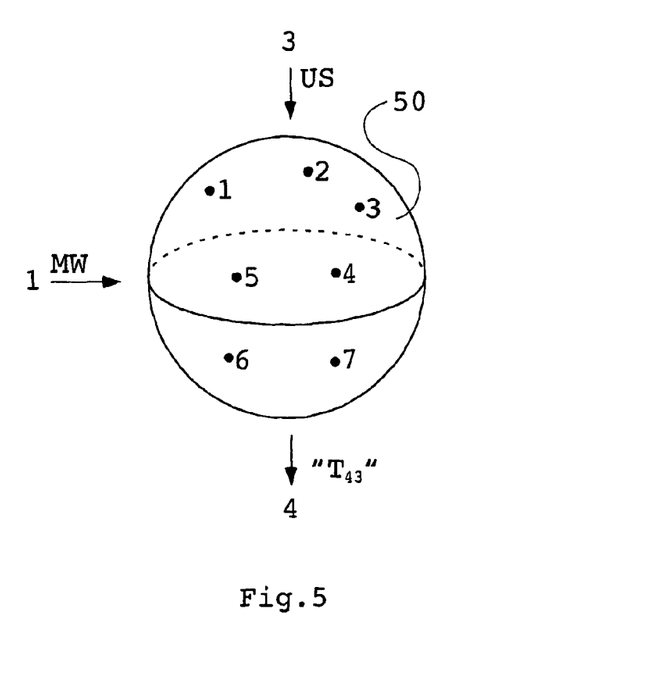
FIG. 5 illustrates an alternative function of the method according to the present invention.

FIG. 5 illustrates a modified embodiment of the method according to the invention. A product 50 is radiated with microwave radiation from a microwave transmitter 1 and ultrasonic radiation from an ultrasound transducer 3. An ultrasonic receiver 4 will be able to determine $T_{43}$ as described in FIG. 2 using an analogue/digital converter 5 and a signal processor 6. No microwave receiver is present and the product is stationary during the measurement. The ultrasonic radiation is focused on a number of points inside the product 50, marked "1", "2", "3", "4", "5", "6" and "7". A determination of the values for $Re(T_{43})$ and $Im(T_{43})$ is made for each focal point and the result is presented in a pseudo-Poincaré curve 60 with a starting point marked "0", which represent the absence of a product in the measurement gap.

Figure 7:
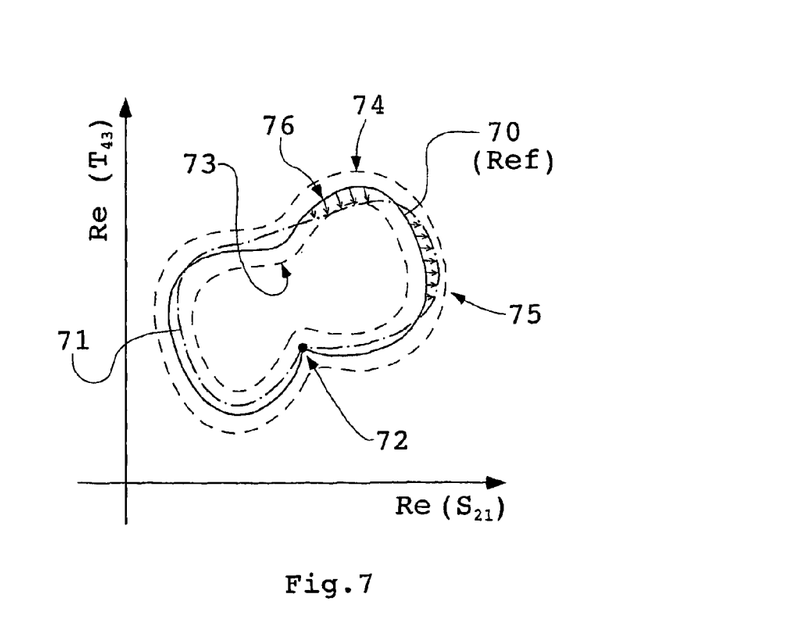
FIG. 7 illustrates how a change in material composition in a product under examination is detected according to the invention.

So far we have described the system needed to obtain an image which represents the material composition of product under examination. FIG. 7 illustrates how a change in material composition in a product under examination can be detected. In the evaluation unit 18; 25 in FIGS. 1 and 2, respectively, a two-dimensional Poincaré curve is generated and a reference curve is retrieved from a memory, such as the reference database 19.

The solid line 70 represents the reference curve from the database 19 and the dash-dot line 71 represents the measured and calculated Poincaré curve. Point 72 represents the absence of a product in the measurement gap. There is normally a discrepancy, as is obvious from the figure, between the reference curve 70 and the calculated curve 71, and there is a need to establish a maximum allowed difference between the curves. The dashed curves 73 and 74 indicate the maximum allowed deviation from the reference curve 70. In the area 75, the calculated curve 71 is well within the allowed limits, but in the area 76, the calculated curve 71 crosses the maximum allowed deviation from the reference curve 70. The product under examination thus shows a change in material composition that lies outside the predetermined limits, and the product is rejected. If the calculated curve 71 i.e. within the dashed curves 73 and 74, the product will be accepted and the calculated values may be used to update the reference curve as will be described in more detail below.

The small arrows in the areas 75 and 76 represent the measurement points used to create the different curves. Several thousands of measurement points are normally used.

Figure 8:
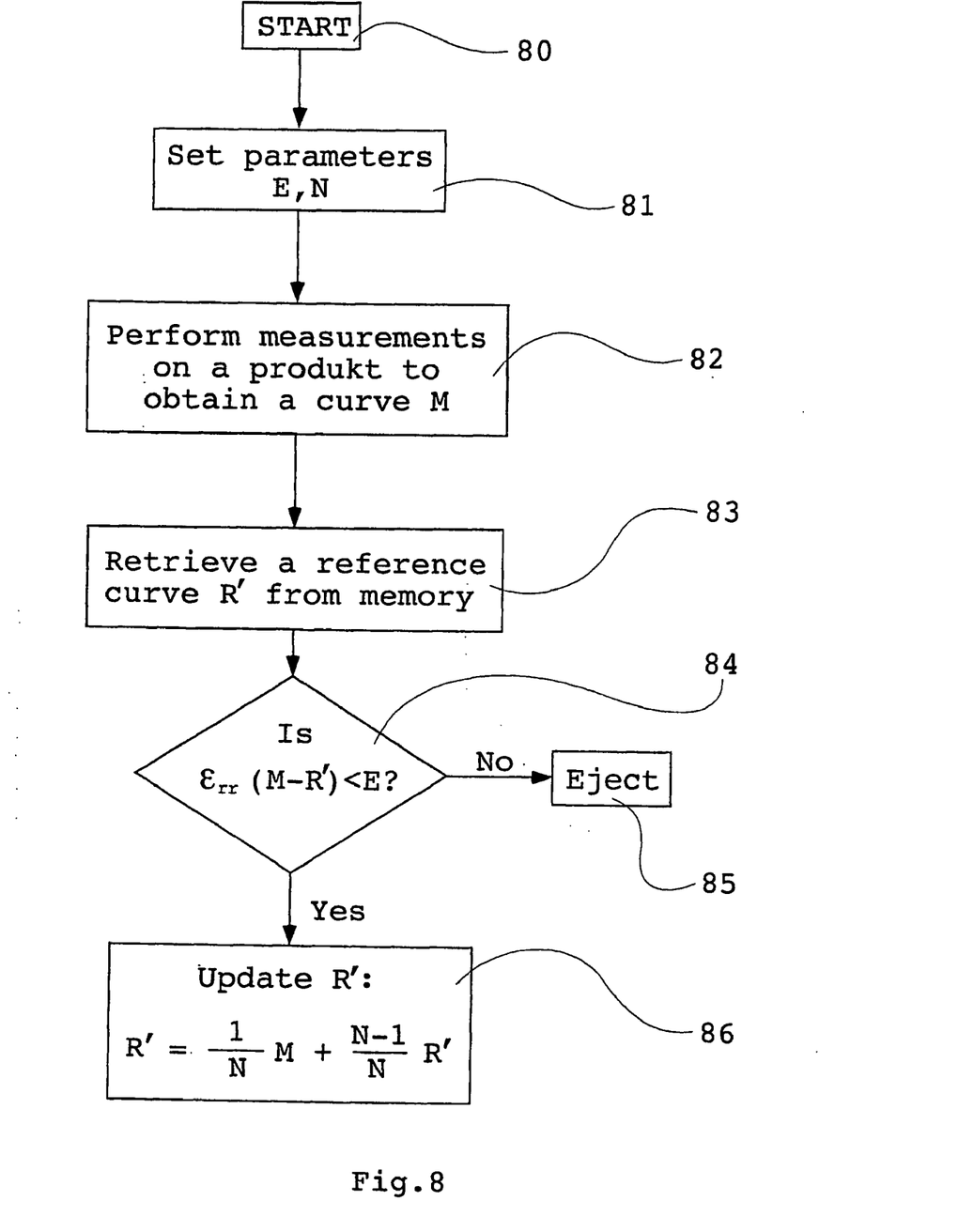
FIG. 8 shows a flow chart of a first embodiment of the process for detecting of a change in material composition.

FIG. 8 shows a flow chart of a first embodiment of the process for detecting a change in material composition. The flow starts at step 80, and in step 81 certain parameters are set. The parameter N, which is the number of measurements used to determine the reference values, is preferably more than 100 up to several thousands (e.g. 2000), and in this example N is set to 150. E is the maximum allowed deviation from the reference curve, which could be an absolute value or a percentage.

In step 82, the measurements on a product are performed to obtain a curve M as described earlier, and in step 83 a reference curve R' is retrieved from a memory e.g. the reference (database).

In step 84, an error function, $\in rr(M-R')$, between the obtained curve M and the reference curve R' is calculated for every measurement point on the curves, and is compared with the allowed deviation E. If the error function is greater than the maximum allowed deviation in any measurement point on the curve, the product is rejected and as a result, the product is ejected from the conveyor means, step 85.

On the other hand, if the error function is less than the maximum allowed deviation in any measurement point, the process proceeds to step 86. The product is accepted and is retained on the conveyor means to be packed and shipped to the consumers. In step 86, the reference curve R' is updated using the values from curve M, as they represent an allowed product, using the formula:

$$R' = \frac{1}{N}M + \frac{N-1}{N}R'$$

The flow is fed back to step 82 to proceed with a new measurement on another product, unless there is a desire to change the parameters in step 81.

Figure 9:
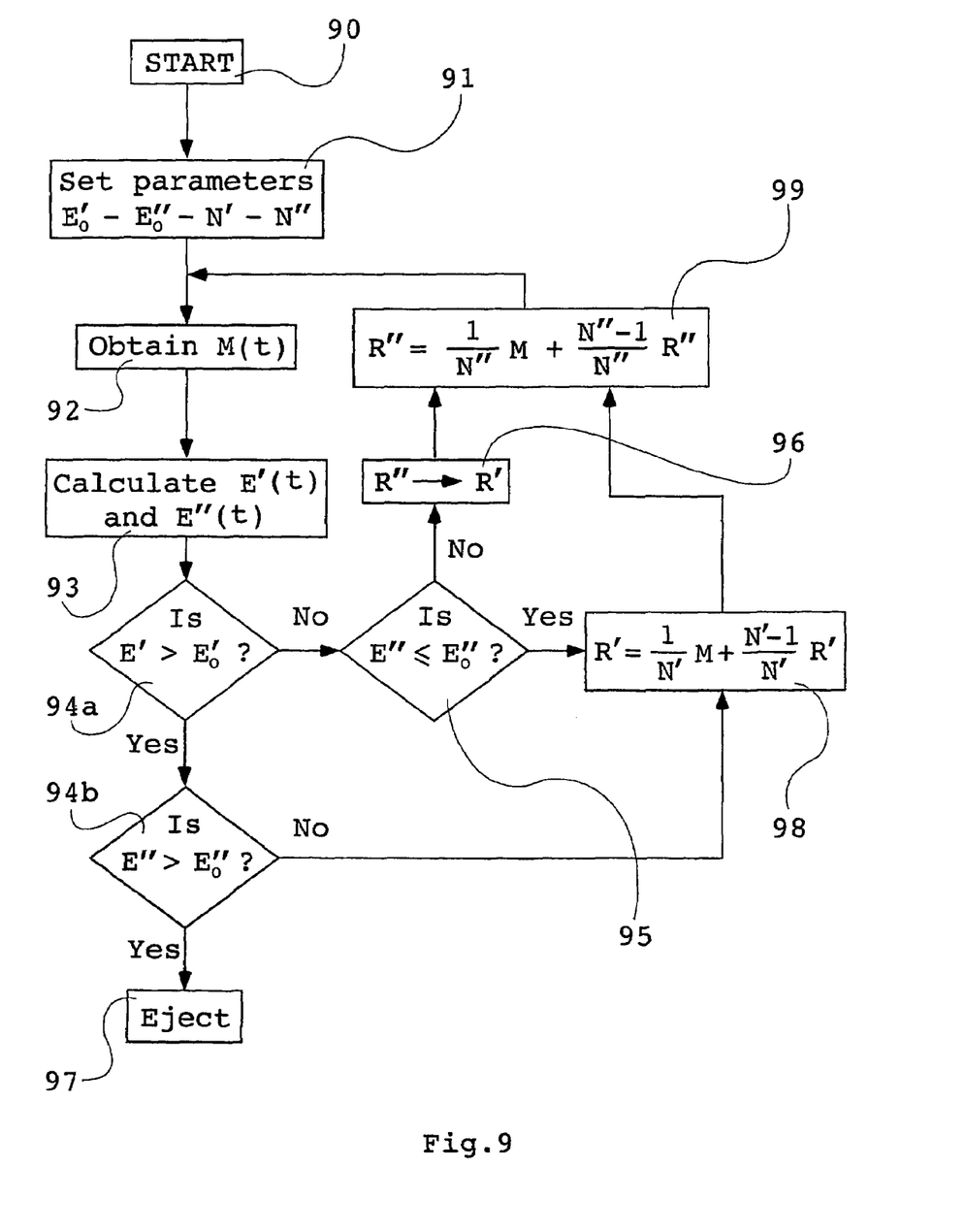
FIG. 9 shows a flow chart of a second embodiment of the process for detecting of a change in material composition.

FIG. 9 shows a flow chart of a second embodiment of the process for detecting a change in material composition that is more advanced, but the basic function is still the same. The flow starts at step 90, and in step 91 certain parameters are set. N', which is the number of measurements used to determine the reference values, is preferably more than 100 up to several thousands (e.g. 2000), and in this example N' is set to 200. $E_0'$ is the maximum primary allowed deviation from a primary reference curve R' (t), and $E_0''$ is the maximum secondary allowed deviation from a secondary reference curve R" (t). R' (t) and R" (t) could each be an absolute value, or a percentage of each measured value that creates the curve M(t). N" is the number of measurements used to determine if a shift has occurred, and is preferably in the interval 5-20, but is usually set to around 5. It is however important that N"<N'.

In step 92, the measurements on a product is performed to obtain a curve M(t) as described earlier. In step 93 a primary reference curve R'(t) and a secondary reference curve R" (t) are retrieved from a memory (database), and a primary error function E'(t) and a secondary error function E" (t) are calculated using the formulas applying the metric ||:

$E'(t)=|M(t)-R'(t)|$, and $E''(t)=|M(t)-R''(t)|$

In step 94*a*, the primary error function, E' (t) is compared to the allowed primary deviation $E_0'$. If the calculated primary error function is greater than the maximum allowed primary deviation in any measurement point on the curve M(t), the flow proceeds to step 94*b*.

On the other hand, if the primary error function is less than the maximum primary allowed deviation in any measurement point, the process proceeds to step 95. The product is accepted and is retained on the conveyor means to be packed and shipped to the consumers.

In step 94b, the secondary error function, E" (t) is compared to the allowed secondary deviation $E_0$". If the calculated secondary error function is greater than the maximum allowed secondary deviation in any measurement point on the curve M(t), the product is rejected and as a result the product is ejected from the conveyor means, step 97.

On the other hand, if the secondary error function is less than the maximum secondary allowed deviation in any measurement point, the process proceeds to step 98. The product is accepted and is retained on the conveyor means to be packed and shipped to the consumers.

In step 95, the calculated secondary error function E" (t) is compared with the maximum secondary allowed deviation $E_0$", and if the calculated secondary error function is less or equal to the maximum allowed secondary deviation, the process proceeds to step 98. If E" (t) is greater than $E_0$" in any measurement point on curve M, the process proceeds to step 96 where the primary reference curve R' (t) is replaced by the secondary reference curve R" (t) since a shift in material content has occurred, i.e.:

$$R'(t) = R''(t)$$

In step 98, the primary reference is updated since the measured curve M(t) represents an accepted product, using the formula:

$$R'(t) = \frac{1}{N'} M(t) + \frac{N'-1}{N'} R'(t)$$

The process proceeds, from either step 96 or 98, to step 99, where the secondary reference is updated using the formula:

$$R''(t) = \frac{1}{N''} M(t) + \frac{N''-1}{N''} R'(t)$$

The flow is then fed back to step 92 to start a new measurement on another product.

The invention claimed is:

1. A system for detecting a change in material composition in a product, said system comprising:
    at least one microwave transmitter, arranged so as to emit a microwave signal at a predetermined microwave frequency composition, and
    at least one ultrasonic transmitter, arranged so as to emit an ultrasonic signal at a predetermined ultrasonic frequency composition into at least a part of said product to create a propagating density displacement within the product,
    said microwave and ultrasonic transmitters are arranged so as to cause a local interaction between said microwave and ultrasonic signals in at least a part of said product, and said system further comprises:
    receiver means to receive at least one of:
        a) the microwave signal(s) emitted by the microwave transmitter(s) having passed through said part of said product,
        b) the ultrasonic signal(s) emitted by the ultrasound transmitter(s) having passed through said part of said product,
    measurement means to measure the attenuation and/or runtime between each emitted signal and each received signal, respectively, under the influence of said propagating density displacement and the associated interaction, and
    comparison means to compare the measured attenuation and/or runtime with a previously determined attenuation and/or runtime to determine a change in material composition.

2. The system according to claim 1, wherein said ultrasonic transmitter is arranged in contact with the product during measurement.

3. The system according to claim 1, wherein said means to measure the attenuation measures the real and/or the imaginary part of the received microwave and/or ultrasonic signal (s) in relation to the emitted signals.

4. The system according to claim 1, wherein the system further comprises means to generate an at least two-dimensional curve using the measured attenuation and/or runtime relating to a position along the product.

5. The system according to claim 4, wherein said comparison means comprises means to calculate deviating values between the generated curve and a reference curve obtained from a previously determined attenuation, and means to determine if the calculated deviating values exceed a predetermined error value.

6. The system according to claim 1, wherein the system further comprises means to focus said emitted ultrasonic signal(s) to different points inside the product during the measurement of the attenuation.

7. The system according to claim 6, wherein the system further comprises means to generate a measurement value for each focal point, presented in an at least two-dimensional graph using the measured attenuation when focusing the ultrasonic signal.

8. The system according to claim 7, wherein said comparison means comprises means to calculate deviating values between each generated value and a reference value obtained from the previously determined attenuation, and means to determine if the calculated deviating values exceed a predetermined error value.

9. A method for detecting a change in material composition in at least a part of a product, comprising the steps of:
    emitting a microwave signal at a predetermined microwave frequency composition,
    emitting an ultrasonic signal at a predetermined ultrasound frequency composition into said part of said product to create a propagating density displacement within the product,
    receiving at least one of:
        a) the emitted microwave signal(s) having passed through said part of said product,
        b) the emitted ultrasonic signal(s) having passed through said part of said product,
    measuring the attenuation and/or runtime between each emitted signal and each received signal, respectively, under the influence of said propagating density displacement and the associated interaction of said microwave and ultrasonic signals, and
    comparing the measured attenuation and/or runtime with a previously determined attenuation and/or runtime to determine a possible change in material composition in said part of the product.

10. The method according to claim 9, wherein the step of measuring attenuation comprises measuring the real and/or the imaginary part of the received microwave and/or ultrasonic signal(s) in relation to the emitted signals.

11. The method according to claim 9, wherein the method further comprises the step of generating an at least two-dimensional curve using the measured attenuation and/or runtime relating to a position along the product.

12. The method according to claim 11, wherein said step for measuring the attenuation further comprises the steps of calculating deviating values between the generated curve and a reference curve obtained from the previously determined attenuation, and determining if the calculated deviating values exceed a predetermined error value.

13. The method according to claim 9, wherein the method further comprises the step of focusing said emitted ultrasonic signal(s) to different points inside the product during the measurement of the attenuation.

14. The method according to claim 13, wherein said method further comprises the steps of generating a measurement value for each focal point, and presenting them in an at least two-dimensional graph using the measured attenuation when focussing the ultrasound.

15. The method according to claim 14, wherein the step of comparing the measured attenuation comprises the steps of calculating deviating values between each generated value and a reference value obtained from a previously determined attenuation, and determining if the calculated deviating values exceed a predetermined error value.

* * * * *